United States Patent
Herrschaft et al.

(10) Patent No.: US 11,912,554 B1
(45) Date of Patent: Feb. 27, 2024

(54) APPARATUSES AND SYSTEMS FOR THE AUTOMATED RETRIEVAL, TRANSPORT, AND PROCESSING OF ARTICLES

(71) Applicant: MCKESSON CORPORATION, Irving, TX (US)

(72) Inventors: Rich Herrschaft, West Chester, PA (US); Jason Warner, Downingtown, PA (US)

(73) Assignee: MCKESSON CORPORATION, Irving, TX (US)

( * ) Notice: Subject to any disclaimer, the term of this patent is extended or adjusted under 35 U.S.C. 154(b) by 405 days.

(21) Appl. No.: 16/832,007

(22) Filed: Mar. 27, 2020

(51) Int. Cl.
| | |
|---|---|
| *B65B 7/16* | (2006.01) |
| *B65B 7/28* | (2006.01) |
| *B65B 57/00* | (2006.01) |
| *B67B 3/26* | (2006.01) |
| *H04W 4/80* | (2018.01) |
| *B67B 3/20* | (2006.01) |

(52) U.S. Cl.
CPC .............. *B67B 3/264* (2013.01); *B65B 7/16* (2013.01); *B65B 7/28* (2013.01); *B65B 57/00* (2013.01); *B67B 3/2066* (2013.01); *H04W 4/80* (2018.02)

(58) Field of Classification Search
CPC .. B65B 7/16; B65B 7/28; B65B 57/00; B65B 57/02
See application file for complete search history.

(56) References Cited

U.S. PATENT DOCUMENTS

| | | | |
|---|---|---|---|
| 4,773,204 A * | 9/1988 | Rydstrom | B67B 3/26 53/313 |
| 5,528,925 A * | 6/1996 | Sherepa | B65B 57/18 73/49.3 |
| 6,237,418 B1 * | 5/2001 | Coughlin | B67B 3/26 209/524 |
| 6,256,967 B1 * | 7/2001 | Hebron | G07F 17/0042 53/437 |
| 6,317,648 B1 * | 11/2001 | Sleep | B65B 65/003 53/500 |
| 7,669,707 B2 * | 3/2010 | Kenneway | B07C 5/02 198/398 |
| 8,745,961 B2 * | 6/2014 | Terzini | A61J 7/02 53/247 |
| 9,150,399 B2 * | 10/2015 | Michelli | B67C 7/00 |
| 9,514,131 B1 * | 12/2016 | Bochenko | G16H 10/40 |
| 9,776,754 B2 * | 10/2017 | Mahar | B65B 7/2842 |
| 2003/0009984 A1 * | 1/2003 | Baskin | B65B 57/02 53/75 |

(Continued)

*Primary Examiner* — Thomas M Wittenschlaeger
*Assistant Examiner* — Katie L Gerth
(74) *Attorney, Agent, or Firm* — Ballard Spahr LLP

(57) ABSTRACT

A method and apparatus for dispensing and retrieving products is provided. A system may include: a grasping head; first and second grasping members, each grasping member comprising: a top member; a post member; and first and second grasping fingers, where the first and second grasping fingers extend from the post member and are spaced apart from the top member by a predetermined distance, where the first and second grasping members are connected to the grasping head, where at least one of the first and second grasping members is movably connected to the grasping head, where the at least one of the first and second grasping members is movable relative to the other of the first and second grasping members.

10 Claims, 8 Drawing Sheets

(56) References Cited

U.S. PATENT DOCUMENTS

| | | | | |
|---|---|---|---|---|
| 2010/0037557 A1* | 2/2010 | Wilhelm | ............... | B65B 7/2807 |
| | | | | 53/331.5 |
| 2011/0016833 A1* | 1/2011 | Carlson | .................. | B65B 57/12 |
| | | | | 53/473 |
| 2016/0355291 A1* | 12/2016 | Mahar | ................... | B65B 7/2807 |
| 2018/0105294 A1* | 4/2018 | Abboud | ................. | B65B 3/003 |

* cited by examiner

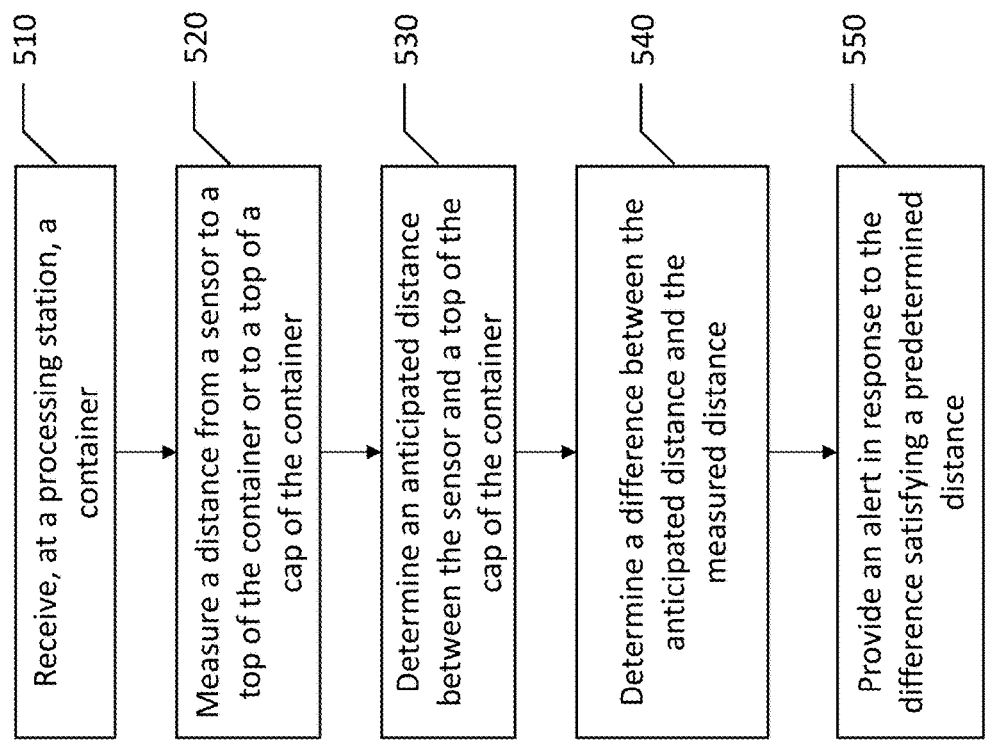

APPARATUSES AND SYSTEMS FOR THE AUTOMATED RETRIEVAL, TRANSPORT, AND PROCESSING OF ARTICLES

TECHNOLOGICAL FIELD

Embodiments of the present invention relate generally to automated retrieval, transport, and processing of articles, and in particular, to an apparatus configured to detect properties of a dispensed article as it is processed within an automated dispensing system.

BACKGROUND

The dispensing of goods is a common practice that can often be time consuming and prone to error, particularly when performed manually. The automation of dispensing can improve both efficiency and accuracy of the dispensing operation; however, different types of articles necessarily require different types of dispensing. Further, automated dispensing can be costly, and if the dispensing operations are not frequent enough, or there is a low-risk associated with errors, the cost of automation may not be justified.

Automated dispensing and processing may include quality checks along the process to ensure that the proper article have been dispensed and they are in their proper form. These quality checks may be performed manually; however, manual quality checks are subject to human error. Other forms of quality checks within a dispensing and processing system may improve the quality and consistency of products that are dispensed and processed. These improvements may benefit quality, efficiency, safety, and reliability of the dispensing and processing system.

SUMMARY

Embodiments of the present disclosure may provide a method, apparatus, and system for retrieving, dispensing, and processing articles. An example method provided herein includes: receiving, at a processing station, a container, where the processing station receives the container along a processing line; measuring a distance from at least one sensor of the processing station to a top of the container in response to the container not including a cap thereon, or a top of a cap of the container in response to the container including a cap thereon, where the at least one sensor is positioned above the processing line; determining an anticipated distance between the at least one sensor and the top of the cap of the container; determining a difference between the anticipated distance and the measured distance; and providing an alert in response to the difference satisfying a predetermined distance.

Methods may include: identifying the container received at the processing station; identifying a cap type corresponding to the identified container; and establishing the anticipated distance between the at least one sensor and the top of the cap of the container based on the identified container and the identified cap type. The predetermined distance may be a first predetermined distance, where providing an alert in response to the difference satisfying the first predetermined distance may include: providing an alert of a missing cap in response to the difference satisfying a first predetermined distance. Methods may include providing an alert of an unseated cap in response to the difference satisfying a second predetermined distance. Methods may include providing an alert of at least one of a wrong container type or a wrong cap type in response to the difference satisfying a third predetermined distance.

According to an example embodiment, the container received at the processing station is received within a container puck, where the container puck includes a unique identifier. Methods may include: reading the unique identifier of the container puck along the processing line; identifying the container based on the unique identifier of the container puck; and identifying a cap type based on the unique identifier of the container puck. Identifying the container based on the unique identifier of the container puck and identifying the cap type based on the unique identifier of the container puck may include determining, from a memory, an identification of the container and an identification of the cap type based on a correlation between the container puck and the identification of the container and the identification of the cap type. Methods may include: establishing the anticipated distance between the at least one sensor and the top of the cap of the container based on the identification of the container and the identification of the cap type. Methods may include: correlating the unique identifier of the container puck with the identification of the container and the identification of the cap type in response to a dispensing operation upstream of the processing station; and storing the correlation between the unique identifier of the container puck with the identification of the container and the identification of the cap type in a memory.

Embodiments of the present disclosure may include a system including: a controller; at least one sensor; a processing line; and a container disposed between the at least one sensor and the processing line, where the at least one sensor measures a distance between one of a top of the container and the at least one sensor or a cap positioned on the top of the container and the at least one sensor, where the controller identifies an anticipated distance between the at least one sensor and a cap on top of the container, where the controller determines a difference between the anticipated distance and the distance between one of the top of the container and the at least one sensor or the cap positioned on the top of the container and the at least one sensor, and where the controller provides an alert in response to the difference satisfying a predetermined distance.

According to an example embodiment, the system may include a container puck carrying the container and disposed between the container and the processing line, where the container puck includes a unique identifier in the form of a radio frequency identification (RFID) tag. The system may include an RFID reader, where the RFID reader is configured to read the unique identifier of the container puck on the processing line, where the controller is configured to identify the container and the cap type based on the unique identifier of the container puck. The controller may be configured to calculate the anticipated distance between the at least one sensor and the cap on the top of the container based on the identified container and cap type. The controller may be configured to identify a sensor of the at least one sensor based on the identified container and cap type to measure a distance between one of a top of the container and the sensor or a cap positioned on top of the container and the sensor. The controller may be configured to store a correlation between the container puck, the identification of the container, and the cap type in response to a dispensing operation upstream of the processing line.

Embodiments provided herein may include an apparatus having at least one processor and at least one memory including computer program code, the at least one memory and computer program code configured to, with the processor, cause the apparatus to: receive at a processing station, a container, where the processing station receives the container along a processing line; measure a distance from at least one sensor of the processing station to a top of the container in response to the container not including a cap thereon, or a cap of the container in response to the container including a cap thereon, where the at least one sensor may be positioned above the processing line; determine an anticipated distance between the at least one sensor to a top of the cap of the container; determine a difference between the anticipated distance and the measured distance from the at least one sensor of the processing station to the top of the container in response to the container not including a cap thereon or a top of a cap of the container in response to the container including a cap thereon; and provide an alert in response to the difference satisfying a predetermined distance.

The apparatus of an example embodiment may be caused to: identify the container received at the processing station; identify a cap type corresponding to the identified container; and establish the anticipated distance between the at least one sensor and the top of the cap of the container based on the identified container and the identified cap type. The predetermined distance may be a first predetermined distance, where causing the apparatus to provide an alert in response to the difference satisfying a predetermined distance may include causing the apparatus to: provide an alert of a missing cap in response to the difference satisfying the first predetermined distance. The apparatus may be caused to provide an alert of an unseated cap in response to the difference satisfying a second predetermined distance.

DESCRIPTION OF THE DRAWINGS

Reference now will be made to the accompanying drawings, which are not necessarily drawn to scale, and wherein:

FIG. 8 is a flowchart of a method for processing of a dispensed container according to an example embodiment of the present disclosure.

DETAILED DESCRIPTION

Figure 1:
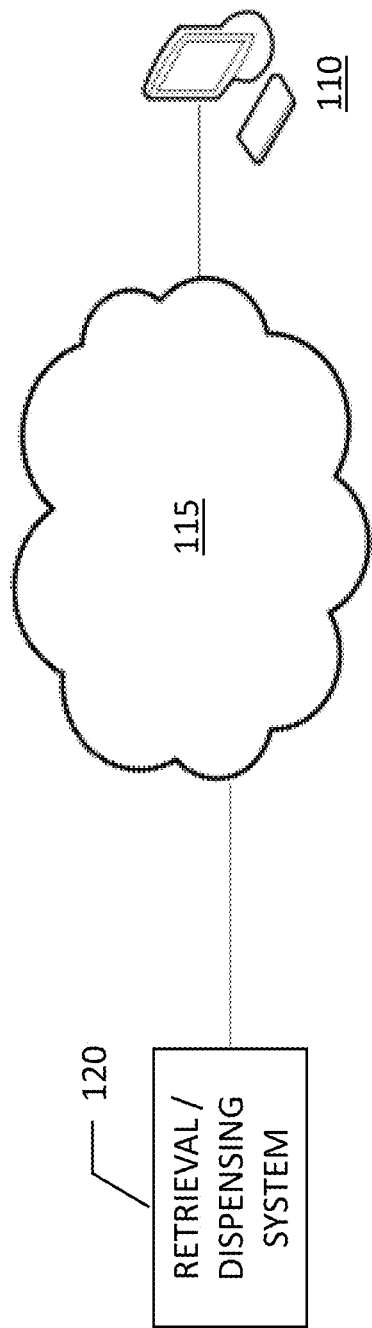
FIG. 1 illustrates a schematic of an automated retrieval, dispensing, and processing system in communication with a user station via a network according to an example embodiment of the present disclosure.

Embodiments of the present disclosure may provide various apparatuses and systems for improving the efficiency with which articles are retrieved, transported, dispensed, and processed. Some embodiments and components of the present disclosure will now be described more fully hereinafter with reference to the accompanying drawings, in which some, but not all embodiments of the disclosure are shown. Indeed, various embodiments of the disclosure may be embodied in many different forms and should not be construed as limited to the embodiments set forth herein; rather, these embodiments are provided so that this disclosure will satisfy applicable legal requirements.

Example embodiments of the present disclosure may provide an apparatus and system to facilitate the automated retrieval, transport, dispensing, and processing of articles, which may be used in a wide variety of applications ranging from industrial manufacturing to precision part procurement to retail distribution. Embodiments may be used in dispensary settings where articles are stored and staged for automated retrieval followed by automated transport and/or dispensing to other areas of a system for processing. Embodiments described herein overcome various challenges of automated retrieval, dispensing, and processing.

Automated retrieval, transport, dispensing, and processing as described herein may improve efficiency and accuracy of dispensing of articles incorporating mechanisms that may solve issues identified by the applicant as substantial hurdles in automating the retrieval, transport, dispensing, and processing of articles, particularly when the articles are of non-uniform sizes. Specifically, embodiments of the present disclosure relate primarily to the processing aspect of such systems and while embodiments are described with respect to complete systems, embodiments described herein may be used as standalone processing stations for processing various types of articles in various industries.

As noted above, systems for automated retrieval, transport, and dispensing may be useful in a wide variety of implementations ranging from industrial applications to retail applications. While systems may be configured to retrieve and transport a wide variety of article form factors, example embodiments described herein focus on a specific form factors including vials and bottles, specifically vials and bottles adapted to contain medications. The vials generally relate to cylindrical tubular containers with an opening to the vial of the same diameter as an inner-diameter of the body of the vial. While bottles are also generally cylindrical, bottles as described herein include a shoulder proximate the top and a bottle opening that is of a smaller diameter than an inner-diameter of the body of the bottle. Both vials and bottles are referred to herein as containers, where containers is interpreted to mean vials and/or bottles. However, containers may come in a variety of sizes, and container caps may be of various configurations. Embodiments described herein are configured to grasp and retrieve for transport a wide variety of container sizes having numerous container cap configurations and sizes.

FIG. 1 depicts a system that can be used in conjunction with various embodiments of the present disclosure. As shown in FIG. 1, an example embodiment of the system may include an automated retrieval/transport/dispensing/processing system 120 and one or more networks 115. As the present disclosure will focus on the processing element of such a system, the retrieval/transport/dispensing/processing system will be referred to herein as a processing system 120 covering both the processing system as part of a larger automated retrieval/transport/dispensing system, or as a standalone processing system that can be modular and may or may not be implemented in such larger systems. Embodiments may include various other devices which may be in communication with the one or more networks 115, such as a user station 110 which may be used for providing manual commands or performing manual review and/or audit of an automated process performed by the processing system 120, for example. Embodiments may further include other network entities from which data may be received from or transmitted to, as will be described further below. Each of the components of the system may be in electronic communication with, for example, one another over the same or different wireless or wired networks (e.g., network 115) including, for example, a wired or wireless Personal Area Network (PAN), Local Area Network (LAN), Metropolitan Area Network (MAN), Wide Area Network (WAN), or the like. Additionally, while FIG. 1 illustrates the system entities as separate, standalone entities, the various embodiments are not limited to this particular architecture.

Figure 2:
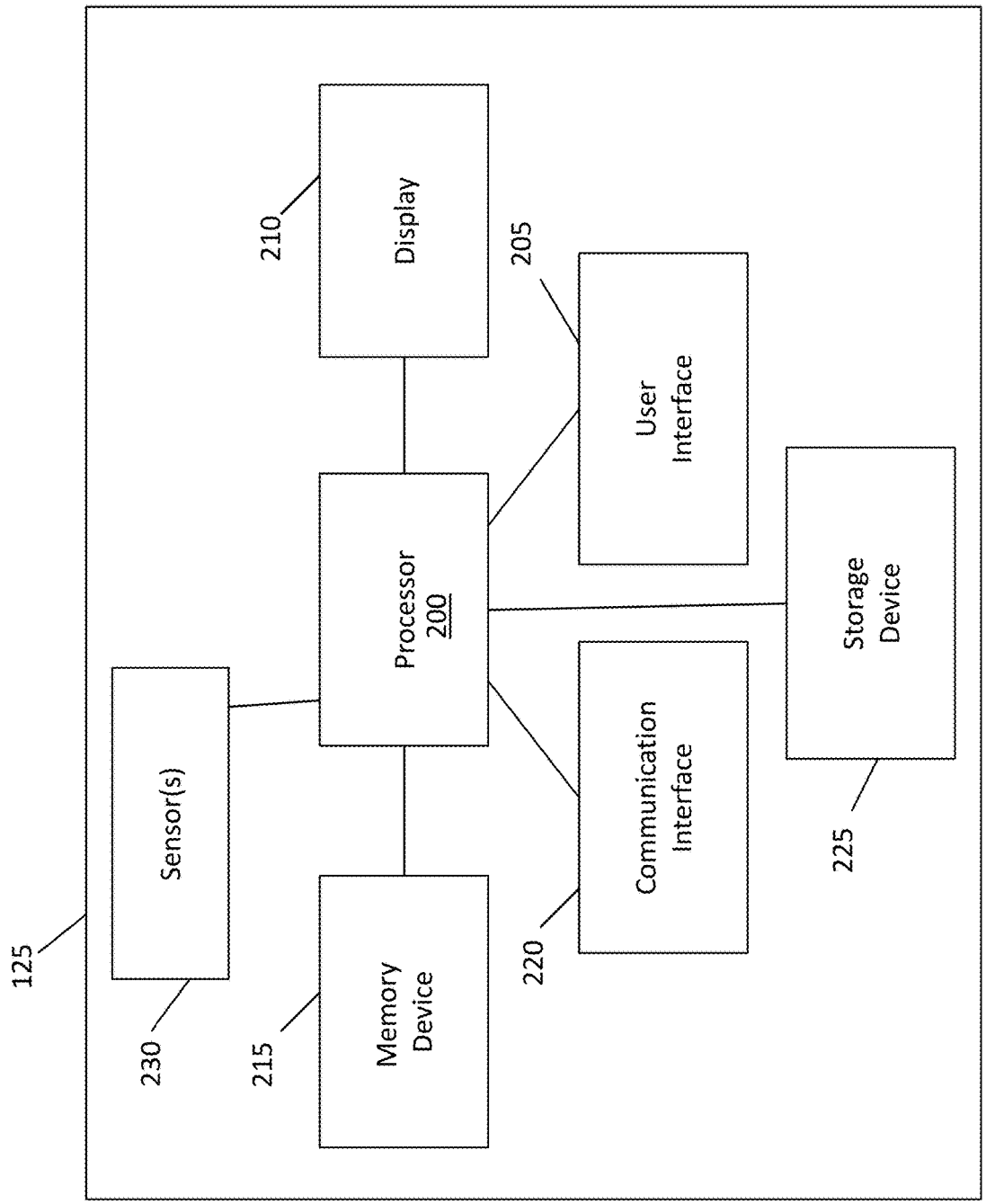
FIG. 2 illustrates a schematic of a controller for controlling an automated retrieval, dispensing, and processing system according to an example embodiment of the present disclosure.

Example embodiments of the processing system 120 as described herein may include a controller configured to control or otherwise facilitate the activities performed at the processing system. FIG. 2 provides a schematic of an example embodiment of a controller 125 of an example processing system. In general, the term "controller" may refer to, for example, any computer, computing device, desktop, tablet, notebook, laptop, distributed system, server, processing device, or combination of processing devices adapted to perform the functions described herein.

In an example embodiment in which the processing system 120 is used for processing medications, the controller 125 may include, be associated with, or be in communication with a variety of computing entities, such as pharmacy inventory management systems, a medication identification database, data storage/facilitation computing entities, or other devices that may interface with inventory management, dispensing, replenishing, etc. While example embodiments of automated processing systems may be implemented in virtually any setting which may benefit from automated dispensing and processing of articles, embodiments described herein will be described generally with respect to the field of healthcare in which medications may be dispensed for patients or caregivers, such as medications packaged in "unit of use" packages which may include containers containing a prescribed quantity of a prescribed medication. However, it is appreciated that embodiments of the present invention may apply to various other embodiments of automated dispensing and processing systems and devices.

As will be understood from FIG. 2, in one embodiment, the controller 125 may include a processor 200 that communicates with other elements of the controller 125 via a system interface or bus. The processor 200 may be embodied in a number of different ways. For example, the processor 200 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an example embodiment, the processor 200 may be configured to execute instructions stored in memory or otherwise accessible to the processor 200. As such, whether configured by hardware or software methods, or by a combination thereof, the processor 200 may represent an entity capable of performing operations according to embodiments of the present invention when configured accordingly. For example, as discussed in more detail below, the controller 125 may be configured to, among other things, facilitate accurate identification of unit of use packages of medication.

A user interface 205 may be configured for user input to initiate the automated retrieval/dispensing process or to confirm, advance, or otherwise interact with operations of the automated retrieval and dispensing process that may interact with processing systems described herein. The user interface 205 may include a keyboard, a pointing device, or other mechanism for a user to communicate with the processor 200 and interact with the controller 125.

A controller according to example embodiments may further include a display 210 which may be configured to present information to a user pertaining to the processing system 120 and to communicate alerts or confirm success of various steps of the process. The display 210 may also be configured to present information to a user pertaining to the status of the processing system, information regarding inventory, or any information which may be useful to a user of the device. The display 210 may include a touch screen display which may partially or fully comprise the user interface 205. According to an example embodiment, the user interface 205 and display 210 may be used for the approval of operations of the process conducted by the processing system, auditing the process, or reviewing alerts from the processing system, for example.

The controller 125 may further include or be in communication with one or more sensor(s) 230. The sensor(s) may include proximity/distance sensors, image capture sensors, radar or LiDAR (light distancing and ranging) sensors, or the like. The sensor(s) 230 of embodiments of the present disclosure may be used to determine the presence of articles and measure a distance of the article from the sensor. Optionally, multiple sensors 230 may be employed to establish a location of an object through triangulation or interpolation of the location established through the sensors 230 and processed by processor 200. The user interface 205, as with any of the components of the controller 125, may be located remotely from the controller 125 and may be accessed via a wired or wireless network.

The controller 125 may further include transitory and non-transitory memory device 215, which may include both random access memory (RAM) and read only memory (ROM). The ROM may be used to store a basic input/output system (BIOS) containing the basic routines that help to transfer information to the different elements within the controller 125.

In addition, in one embodiment, the controller 125 may include or be in communication with at least one storage device 225, such as a hard disk drive, a solid state drive, and/or an optical disk drive for storing information on various computer-readable media. The storage device(s) 225 and its associated computer-readable media may provide non-volatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. The storage device may be configured to store, for example, a list of orders to be retrieved, dispensed, and labeled and/or an audit trail of unit of use packages retrieved, dispensed, and labeled from received orders.

Furthermore, a number of executable instructions, applications, scripts, program modules, and/or the like may be stored by the various storage devices 225 and/or within memory device 215. As discussed in more detail below, these executable instructions, applications, program modules, and/or the like may control certain aspects of the operation of the controller 125 with the assistance of the processor 200 and operating system, although their functionality need not be modularized. In addition to the program modules, the controller 125 may store or be in communication with one or more databases.

Also located within the controller 125, in one embodiment, is a communication interface 220 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. The controller 125 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

Figure 3:
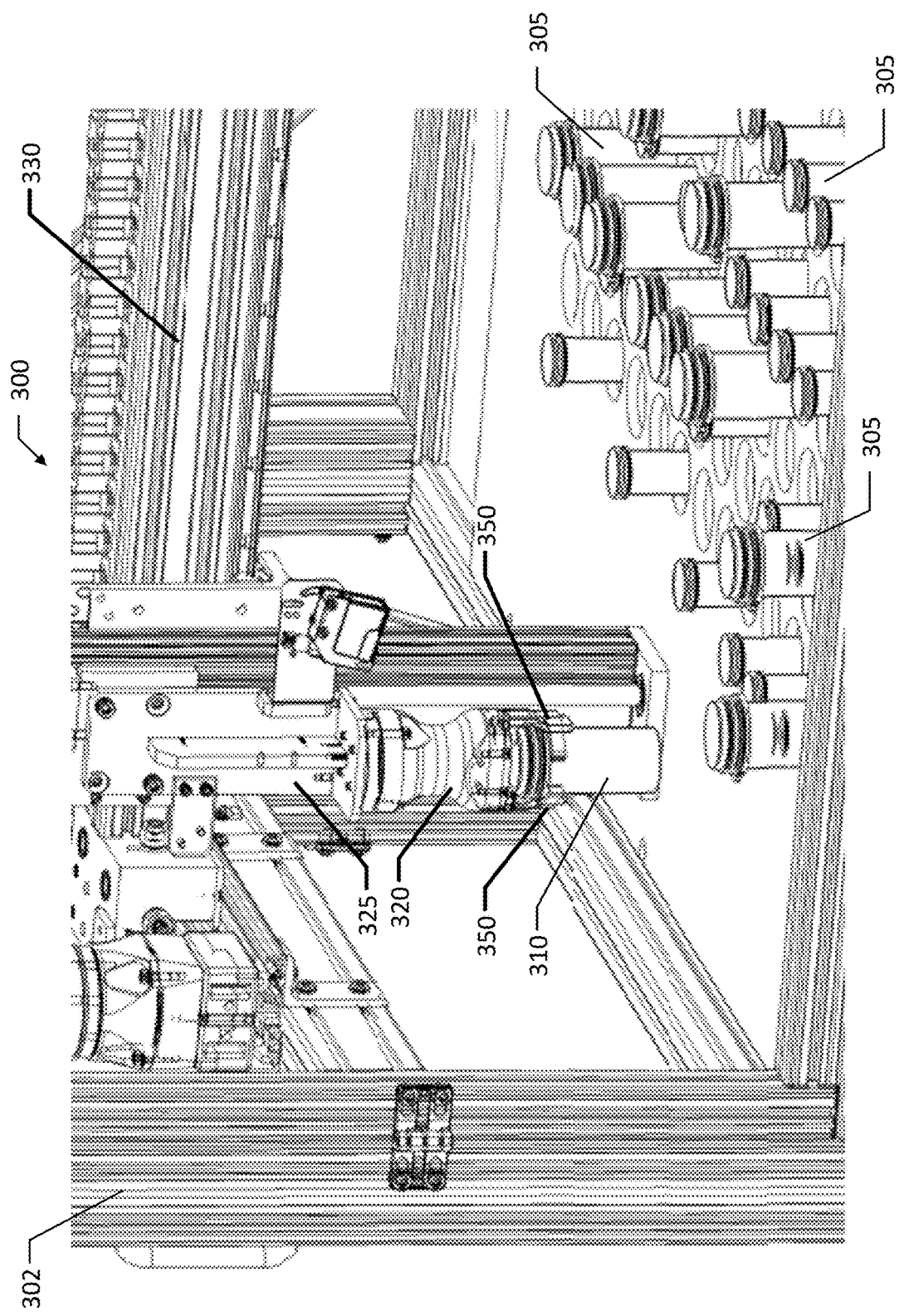
FIG. 3 illustrates an automated retrieval and dispensing system according to an example embodiment of the present disclosure.

In an example embodiment described herein, a processing system may be used to process unit-of-use packaged products dispensed from an automated dispensing system in a variety of environments, such as in a high-volume dispensary for distribution throughout a region. FIG. 3 illustrates an example embodiment of an automated retrieval/transport/dispensing system, or collectively an automated dispensing 300 which may be configured to automatically retrieve and dispense unit-of-use packages of medication in response to receiving a prescription order. Automated dispensing systems 300 which may benefit from example embodiments of the present disclosure may be configured to dispense containers 305 of varying sizes with various cap sizes and configurations as shown. According to the embodiment of FIG. 3, a container 310 may be grasped by grasping members 350, which are attached to a grasping head 320. The grasping head 320 may extend from a robotic arm 325, where the robotic arm 325 is connected to a mechanism for moving the robotic arm 325 within the system 300. The robotic arm 325 of the illustrated embodiment is moved through the system by an X-Y robotic frame 330 that enables the robotic arm 325 to be positioned anywhere within a transport envelope of the robotic frame 330.

Figure 4:
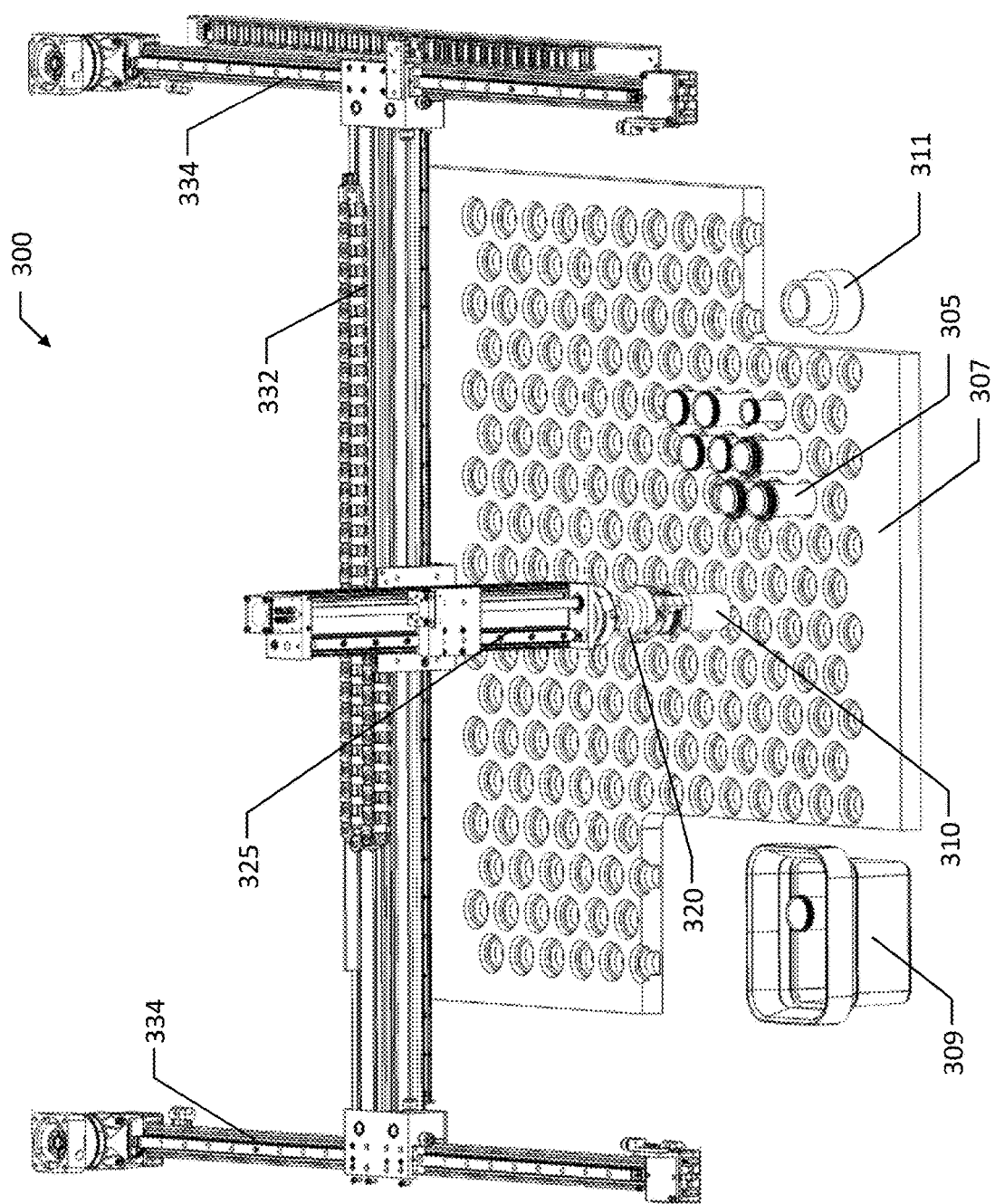
FIG. 4 illustrates an automated retrieval and dispensing system according to another example embodiment of the present disclosure.

FIG. 4 illustrates an example embodiment of the system 300 without the enclosure 302 of FIG. 3 for ease of illustration. As shown, the containers 305 are received within a table 307 having a plurality of container storage locations configured to accommodate containers of various sizes. The robotic arm 325 is attached to an X-Y robotic frame including a transverse member 332 and longitudinal members 334. The robotic head is able to move along a length of the transverse member 332, while the transverse member travels along a length of the longitudinal members 334. This provides overhead access for the robotic arm 325 over an envelope of the system that includes the table 307 and may include stations such as bin station 309 and puck station where a container puck 311 is disposed. The robotic arm 325 is configured to move in a plane orthogonal to the X-Y robot motion, in a Z-axis direction toward and away from the table 307. This movement advances the grasping head 320 toward and away from the containers 305 of the table 307.

Figure 5:
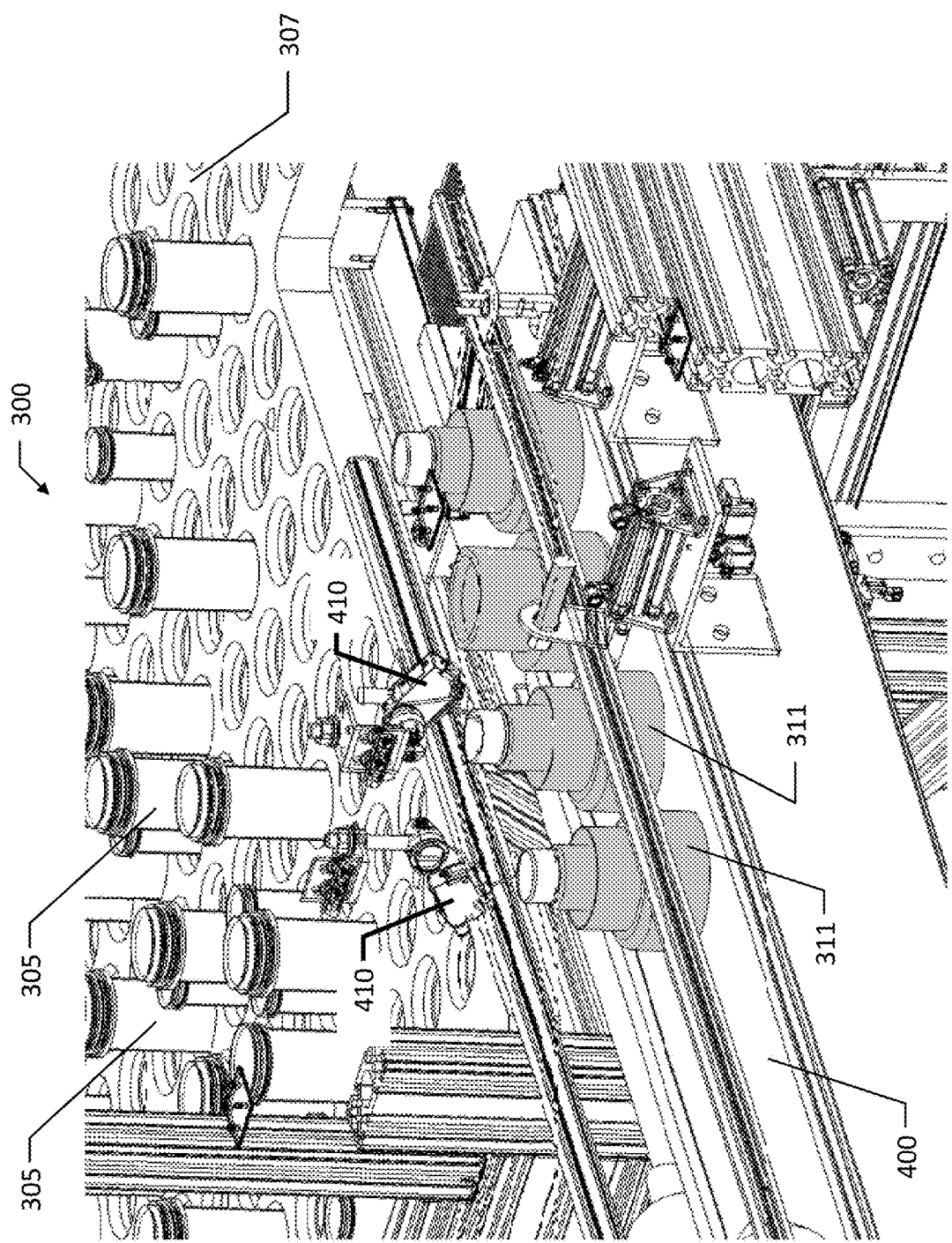
FIG. 5 illustrates a processing portion of an automated retrieval and dispensing system according to an example embodiment of the present disclosure.

FIG. 5 illustrates a processing system to process containers 305 dispensed to the container pucks 311. The processing system of FIG. 5 may be disposed proximate the automated dispensing system 300 shown in FIGS. 3 and 4, such that a retrieved and dispensed container 310 may be dispensed to a container puck 311 in the processing system or processing portion of the automated dispensing system as illustrated. Once the containers are received in respective container pucks 311, the container pucks may be more easily transported for processing as the container pucks have a uniform shape conducive to processing along an automated processing line 400 shown in FIG. 5. Also shown along the processing line 400 of the processing system are sensors 410 disposed above the container pucks 311.

Figure 6:
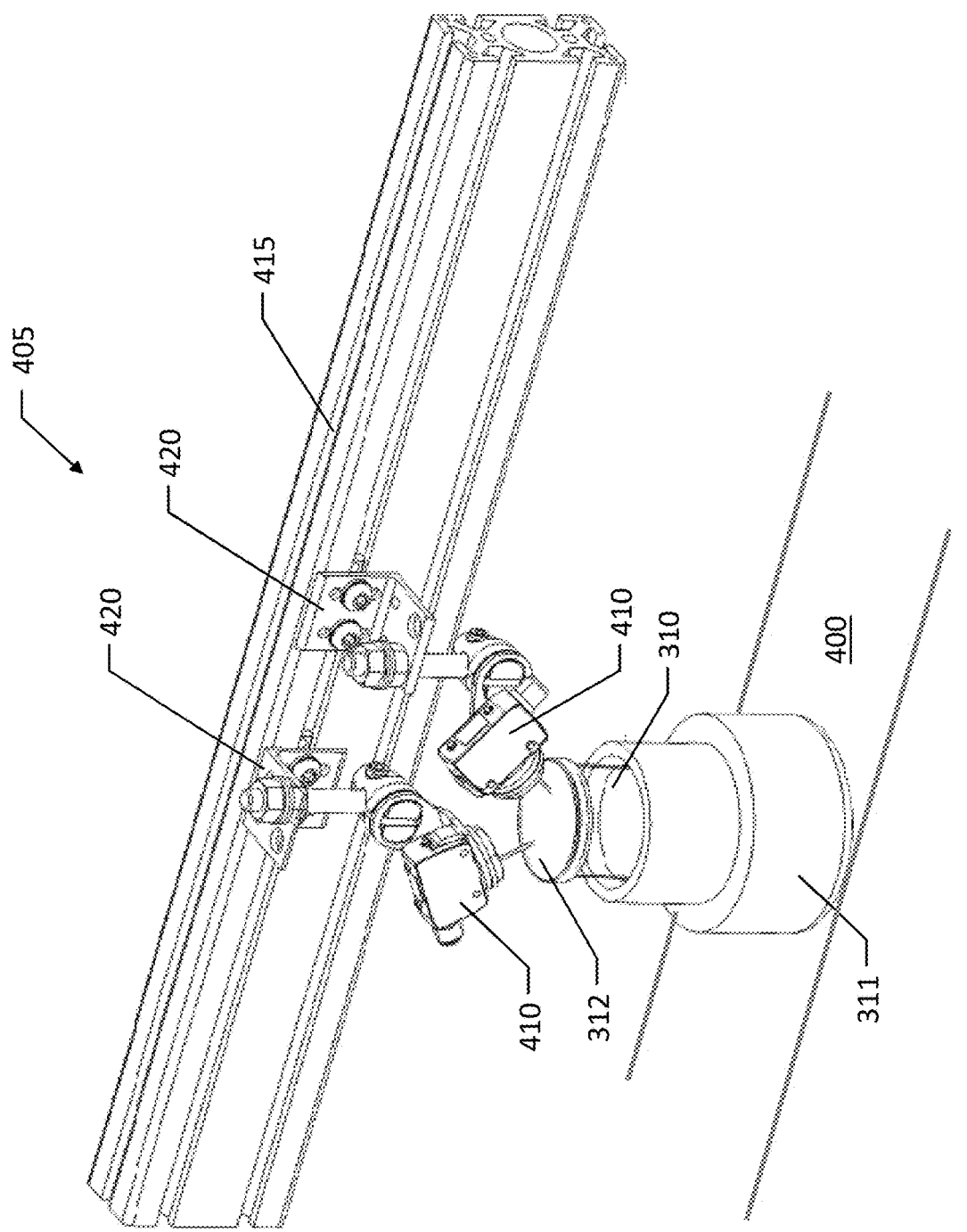
FIG. 6 illustrates a detail view of the processing portion of a processing system according to an example embodiment of the present disclosure.

FIG. 6 illustrates a portion of the processing system extracted from remaining portions of the system for ease of understanding. As shown, a container puck 311 is disposed on a processing line 400, which may, for example, be a conveyor belt, transport bearings (e.g., roller bearings), or other surface along which the container puck 311 can advance. The illustrated portion of the processing system further includes first and second sensors 410 attached by brackets 420 to a structural member 415. The structural member 415, in combination with the brackets 420, may hold the sensors 410 in a substantially fixed position relative to the processing line 400.

As a container puck 311 is advanced along the processing line 400, one or both of the sensors 410 may identify a position of a cap 312 of the container 310. The identification of the cap 312 position may identify whether the cap is properly engaged with the container 310, and may establish if the correct type of cap has been engaged to the container. Containers may be configured to be used with a variety of cap types. For example: a safety cap to preclude children from opening the container; a one-click cap; an easy-open cap for arthritic hands, etc. Further, containers are available in multiple sizes with differing heights. In order for the processing system to determine if the correct cap has been installed on a container, and to determine if the cap has been properly seated and engaged with the container, the processing system must understand what container size and cap type/size to anticipate.

According to example embodiments described herein, the automated dispensing system 300 may receive a request for retrieval and dispensing of a particular article. That article may be associated with a capped container disposed at a predefined location on table 307. The automated dispensing system 300 may retrieve and dispense the capped container 310 to a container puck 311 at the processing line 400. The processing line 400 may then advance the container puck to the processing station of FIG. 6 to determine if the container 310 is properly capped.

The dispensed container 310 may be of a known size based on the controller 125 establishing the container size from the identified container at the identified location on the table 307. When the containers 305 are placed in locations on the table 307, the containers may be uniquely identified, and their respective locations on the table be uniquely identified such that in response to a request received at the controller 125 for a particular type and quantity of medication, the controller can identify a container having that type and quantity of medication based on the information stored in memory 215. The identified container can then be correlated to its recorded location on the table in order to cause the automated dispensing device to retrieve the identified container. Each container stored in table 307 may also have the cap type identified and correlated with the identified container.

Upon dispensing the identified container 310 to the container puck 311, the container puck may be associated with the identified container, such as through a radio frequency identification (RFID) tag on the container puck that is associated at the controller 125 with the identified container 310. This allows the system to identify the container 310 of the container puck 311 by scanning the container puck 311 using an RFID reader. Optionally, the container puck 311 could employ alternative identification means, such as a barcode, QR code, etc.

Upon arrival of the container puck 311 at the processing station 405 of FIG. 6 along processing line 400, the container puck can be identified by a reader, such as an RFID reader. This enables the processing station 405, using controller 125, to identify the container size and cap type of the container that is presently at the processing station. One or both of the sensors 410 may scan the cap of the container as it travels through the processing station 405. The sensors may be configured to scan the cap of the container quickly such that the dwell time of the container puck 311 at the processing station 405 is minimal, and may be on the order of fractions of a second. Further, the container puck 311 may be constantly moving along the processing line 400 such that there is no dwell time, but instead the container puck passes through the processing station 405 in motion without pausing while the sensors 410 scan the cap 312.

Figure 7:
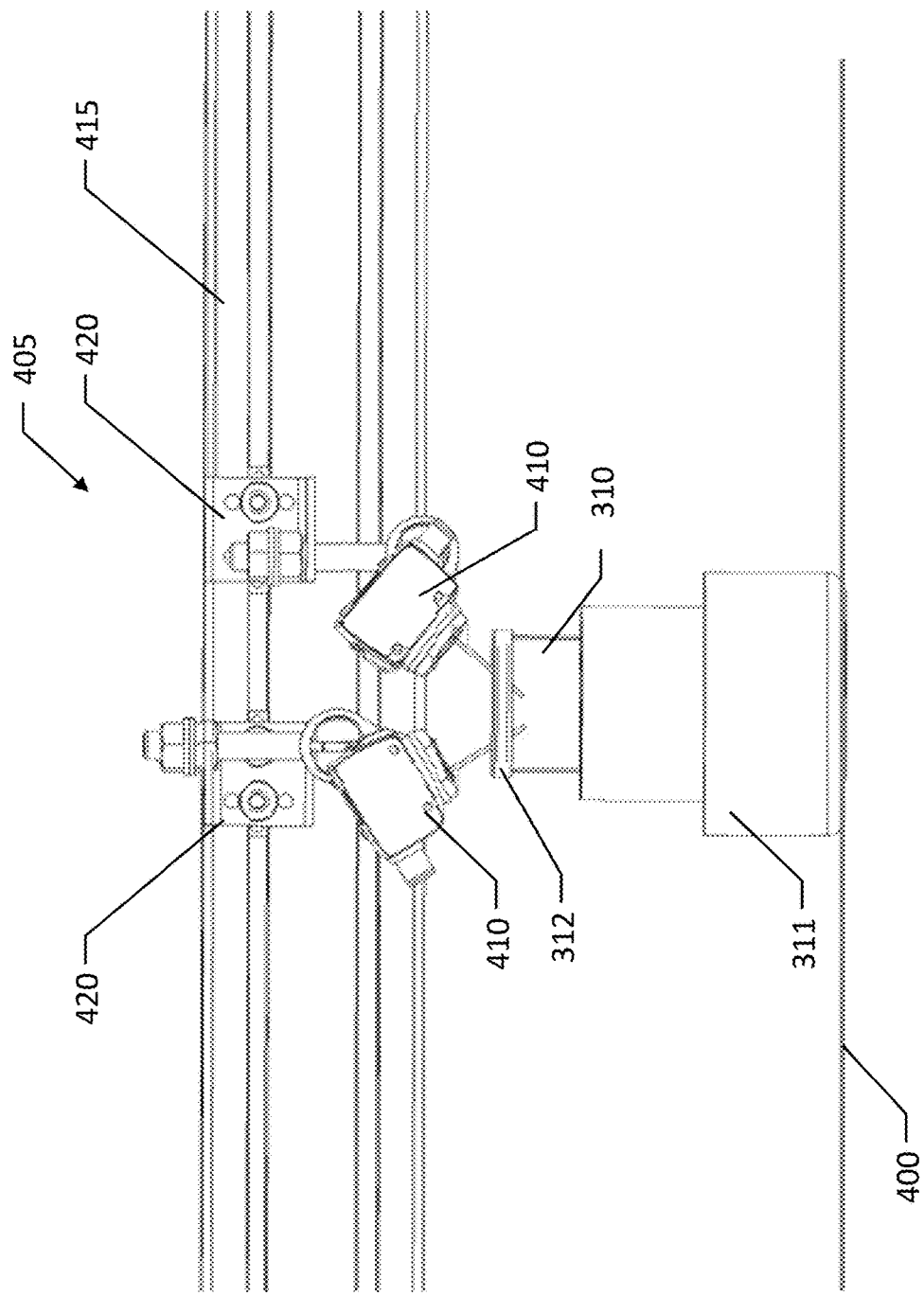
FIG. 7 depicts another detail view of the processing portion of a processing system according to an example embodiment of the present disclosure.

One or more of sensors 410 scan the cap 312 of the container 310 as the container puck 311 passes through the processing station 405. While two sensors are illustrated in the embodiments of FIGS. 6 and 7, more or fewer sensors may be employed. However, certain features described herein may require multiple sensors arranged at different angles with respect to the processing line 400 or a single sensor with the capability of sensing a container cap 312 from multiple angles (e.g., with the use of a mirror or a multi-headed sensor). The one or more sensors 410 may identify a distance of the cap 312 from the respective sensor 410. This distance may be used to establish a cumulative height of the container puck 311, the container 310, and the container cap 312. The container puck may be of a known, fixed height, while the container 310 height may depend upon the size of the container, identified by controller 125. Similarly, the height of the cap 312 may be identified by the controller 125 such that an anticipated cumulative height is established. This anticipated cumulative height may be established before or after the one or more sensors 410 have scanned the cap 312 of the container. The anticipated cumulative height is established with the cap 312 fully seated and engaged with the container 310 such that the container is closed.

The one or more sensors may measure a cumulative height of the container puck 311, the container 310, and the cap 312. This may be performed based on a height of the top of the cap 312 relative to the sensors 410. The height of the sensors 410 from the processing line 400 is fixed such that a cumulative height of the container puck 311, the container 310, and the cap 312 is determined based on a distance of the cap 312 from the one or more sensors 410. If the container cap is at a distance from the one or more sensors 410 resulting in a cumulative height different than that of an anticipated cumulative height by a predetermined value, an alert may be generated, such as by the controller 125.

A height difference between an anticipated cumulative height of the container puck 311, the container 310, and the cap 312 and the measured cumulative height may be indicative of a cap that is not properly seated on the container, an improper cap type, an improper container type, or a combination of these. Any one of these errors can be indicative of a problem that may be significant, such that an alert may be provided to an operator of the processing system, which may be conveyed via user interface 205 and/or display 210 of the controller 125.

The above-described embodiments are directed to measuring the height of a container cap 312 based on a distance from sensors 410. However, embodiments are also enabled to establish when a container cap 312 is not present on a container 310. Such a scenario may be encountered when a container was never capped or lost a cap during prior processing or dispensing. The one or more sensors 410 may detect a container opening by detecting a distance from the sensor substantially greater than anticipated. Such a distance may be indicative of the lack of a cap 312 on a container 310. In such a scenario, an alert may be provided as described above.

While the aforementioned measurements are described with respect to a "cumulative height", the measured dimension is the distance of the cap 312 from the one or more sensors 410. As such, the term "cumulative height" may reference a distance from the sensors 410 due to the fixed relationship between the processing line 400 and the sensors 410. An overall height of the container puck 311, the container 312, and container cap 312 is thus not actually measured, but derived from the distance of the cap 312 from the one or more sensors 410.

Embodiments of the processing station 405 described herein can employ a single sensor 410 to identify a height of the cap 312 relative to the processing line 400. However, multiple sensors may be used for redundancy. For example multiple sensors 410 may be used to measure a height and confirm a height of the cap. Optionally, a first sensor may not achieve a reliable height reading when the processing line 400 is moving quickly, such that sensor redundancy helps reduce the number of unread container caps that may erroneously trigger an alert. Optionally, multiple sensors 410 may be employed for triangulation of a location of the cap 312 for improved accuracy and reliability.

Embodiments described herein may optionally employ different sensors 410 for different type of container caps to be detected. For example, a processing system may be configured to process containers having two different cap configurations. The processing station 410 may employ a single sensor (or pair of sensors) for each of the two different configurations. The sensor(s) 410 that are activated to sense the container cap 312 as a container 310 passes through the processing station 405 in a container puck 311 may be only the sensor configured to sense the particular cap configuration that is anticipated at the processing station. The cap configuration may be associated with the retrieved container 310 and associated with the container puck 311 into which the container is placed. Upon arrival at the processing station, the container puck 311 may be scanned, such as by an RFID scanner, and the anticipated cap configuration may be identified, such as by the controller 125. The appropriate sensor(s) for the specific identified cap configuration may be activated, and may then scan the container 310 and container cap 312 as they pass through the processing station 405. The sensor(s) 410 may then identify any issues, such as if a cap was present or missing, or if the cap was not seated properly. An alert may be generated in response to any identified issue.

Processing stations of example embodiments may include sensors arranged along the processing line 400, adjacent to the processing line and may capture an image of the container puck 311, the container 310, and the container cap 312, and may identify a cumulative height thereof or may use image comparison to determine errors in container sizes, cap sizes, cap types, etc. However, these embodiments employ more costly sensors and require more extensive processing. Embodiments described above with respect to the embodiments of FIGS. 5 through 7 employ more reliable sensors 410 that can repeatably establish a distance to a cap 312 of a container 310 with a high level of efficiency while also reducing the processing capacity required, improving error detection, and reducing cost.

The example embodiment described above using different sensors for different cap configurations may further reduce the cost of the sensors required for a processing station as the sensors may be tuned to a finite window of operation and may not require distance-measuring to the degree necessary for using a single sensor or set of sensors for all cap configurations.

FIG. 8 is a flowchart of a method for processing articles according to an example embodiment of the present disclosure. It will be understood that each block of the flowchart and combinations of blocks in the flowchart may be implemented by various means, such as hardware, firmware, processor, circuitry, and/or other devices associated with execution of software including one or more computer program instructions. These computer program instructions may also be stored in a non-transitory computer-readable memory that may direct a computer or other programmable apparatus to function in a particular manner, such that the instructions stored in the computer-readable memory produce an article of manufacture which implements the functions specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the disclosure, as shown in FIG. 8, may include receiving, at a processing station, a container as shown at 510. The processing station may receive the container along a processing line, and the container may be within an object that facilitates transport along the processing line, such as a container puck which may be a uniform form factor to carry containers of varying sizes. At 520, a distance is measured from a sensor to a top of the container in the case of an uncapped container or to a top of a cap on the container in the case of a capped container. An anticipated distance between the sensor and the top of the cap of the container is established at 530. A difference between the anticipated distance and the measured distance is determined at 540. In response to the difference satisfying a predetermined distance, an alert is provided at 550.

Moreover, in some embodiments additional operations may also be included. It should be appreciated that each of the modifications, optional additions, or amplifications may be included with the operations above either alone or in combination with any others among the features described herein.

In an example embodiment, an apparatus for performing the method of FIG. 8 may include a processor, such as processor 200 of controller 125, configured to perform some or all of the operations (510-550) described above. The processor may, for example, be configured to perform the operations (510-550) by performing hardware implemented logical functions executing stored instructions, or executing algorithms for performing each of the operations. Alternatively, the apparatus may include means for performing each of the operations described above.

An example of an apparatus according to an example embodiment may include at least one processor and at least one memory including computer program code. The at least one memory and the computer program code may be configured to, with the at least one processor, cause the apparatus to perform the operations 510-550.

An example of a computer program product according to an example embodiment may include at least one computer-readable storage medium having computer-executable program code portions stored therein. The computer-executable program code portions may include program code instructions for performing operations 510-550.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
    receiving, at a processing station, a container, wherein the processing station receives the container along a processing line;
    determining, based on a type of the container, a first cap type of a plurality of cap types, wherein each cap type of the plurality of cap types is associated with a corresponding cap size;
    measuring a distance from at least one sensor of the processing station to a top of a cap of the container, wherein the at least one sensor is positioned above the processing line;

determining, based on the type of the container and the cap size corresponding to the first cap type, an anticipated distance between the at least one sensor and the top of the cap;

determining a difference between the anticipated distance and the measured distance, wherein the difference satisfying a first predetermined distance is indicative of the cap being improperly seated on the container, and wherein the difference not satisfying the first predetermined distance is indicative of the cap being properly seated on the container;

determining that the difference satisfies the first predetermined distance; and providing an alert of the cap being improperly seated on the container in response to the difference satisfying the first predetermined distance.

2. The method of claim 1, further comprising:

identifying the type of the container received at the processing station;

identifying the first cap type corresponding to the type of the container; and establishing the anticipated distance between the at least one sensor and the top of the cap based on the type of the container and the first cap type.

3. The method of claim 1, further comprising:

determining a second difference between a second anticipated distance and a second measured distance associated with a second container.

4. The method of claim 3, further comprising:

providing, based on the second difference, an alert of an improperly seated cap.

5. The method of claim 3, further comprising:

providing, based on the second difference, an alert of at least one of a wrong container type or a wrong cap type.

6. The method of claim 1, wherein the container received at the processing station is received within a container puck, and wherein the container puck comprises a unique identifier.

7. The method of claim 6, further comprising:

reading the unique identifier of the container puck;

identifying the type of the container based on the unique identifier of the container puck; and identifying the first cap type based on the unique identifier of the container puck.

8. The method of claim 7, wherein identifying the type of the container based on the unique identifier of the container puck and identifying the first cap type based on the unique identifier of the container puck comprises:

determining the type of the container and the first cap type based on an association between: the unique identifier of the container puck, the type of the container, and the first cap type.

9. The method of claim 8, further comprising:

establishing the anticipated distance based on the type of the container and the first cap type.

10. The method of claim 7, further comprising:

associating the unique identifier of the container puck with the type of the container and the first cap type in response to a dispensing operation upstream of the processing station; and storing, in memory, an association between the unique identifier of the container puck with the type of the container and the first cap type.

* * * * *